Figure 1:
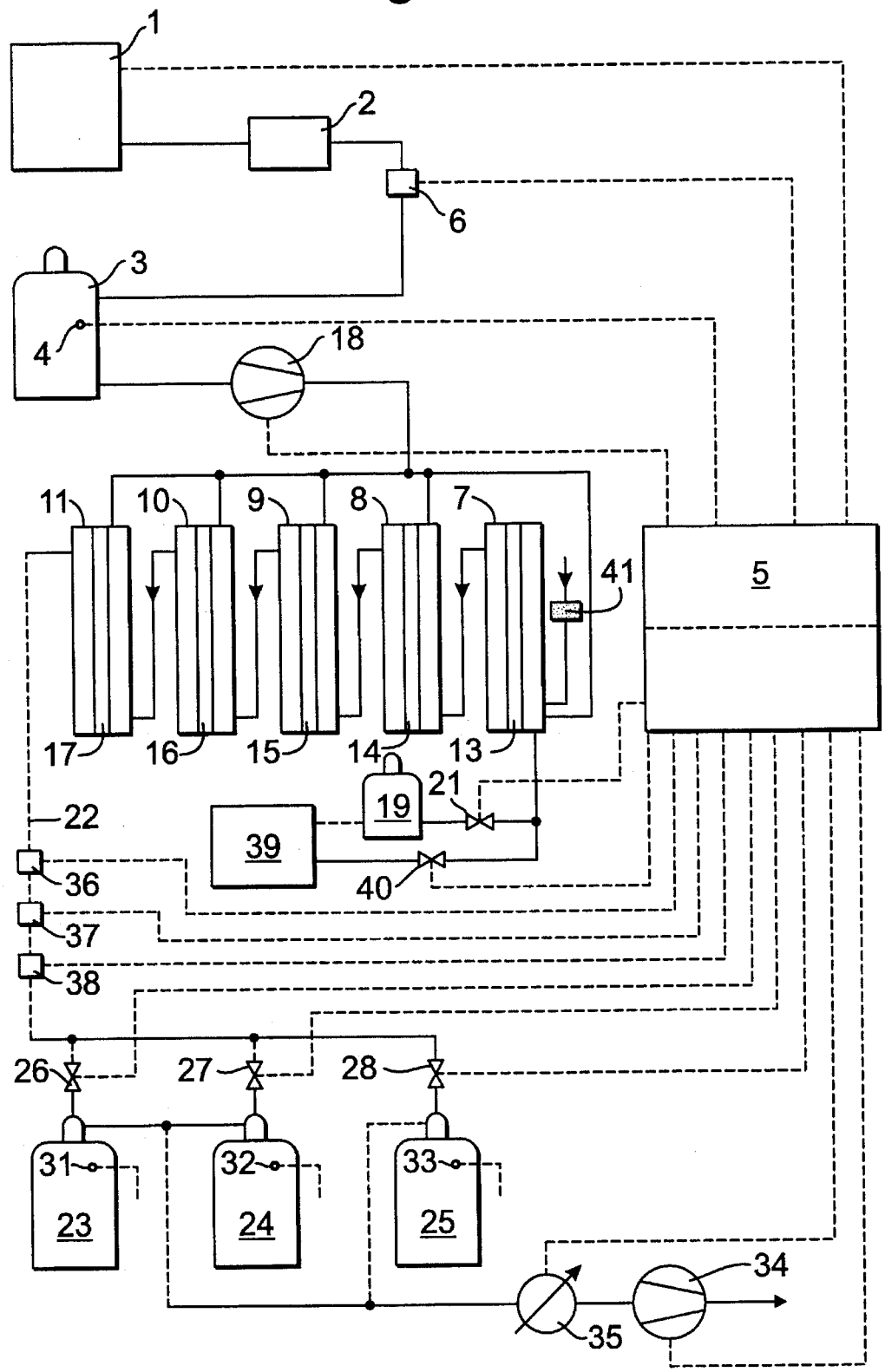

United States Patent [19]
Renschler et al.

[11] Patent Number: 5,603,962
[45] Date of Patent: Feb. 18, 1997

[54] USE OF AQUEOUS SOLUTIONS CONTAINING PEROXOBISULPHATE IONS FOR THE TREATMENT OF MALIGNANT CELLS

[75] Inventors: Aloys Renschler, Neusser Strasse 201, 50733 Koln; Dieter Schuster, Wuppertal, both of Germany

[73] Assignee: Aloys Renschler, Cologne, Germany

[21] Appl. No.: 256,370

[22] PCT Filed: Sep. 29, 1992

[86] PCT No.: PCT/EP92/02244

§ 371 Date: Oct. 20, 1994

§ 102(e) Date: Oct. 20, 1994

[87] PCT Pub. No.: WO93/14774

PCT Pub. Date: Aug. 5, 1993

[30] Foreign Application Priority Data

Jan. 24, 1992 [DE] Germany .......................... 42 01 858.7

[51] Int. Cl.⁶ .......................... A61K 33/40; A61K 41/00; A61N 5/06
[52] U.S. Cl. .............................................................. 424/613
[58] Field of Search ............................................. 424/613

[56] References Cited

FOREIGN PATENT DOCUMENTS

| 2316923 | 4/1977 | France . |
|---|---|---|
| 3528379A1 | 12/1987 | Germany . |

OTHER PUBLICATIONS

Chemical Abstracts, vol. 96, 1982, Columbus, Ohio, US; Abstract No. 173681h, p. 2, col. 1, Vannikov L. L. "Antihypoxic Effect of PSN," Tkanevaya Gipoksiya EEE Korrekts 1981, pp. 4–27.
Chemical Abstracts, vol. 67, 1967, Columbus, Ohio, US; Abstract No. 8451b, p. 787, col. 2, A. M. Lokshina et al. "The radiosensitizing Action of Sodium Persulfate," Med. Radiol., vol. 12, No. 2, 1967, pp. 81–83.
Derwent Publications Ltd., London, GB; AN 86026462(04) PT, A, 80 707 (Colgate Palmolive Co.,) 6 Dec. 1985.
Warburg, O., "Partielle Anaerobiose der Krebszellen und Workung der Rontgenstrahlen auf Krebszellen," *Naturwissenschafen*, 46:25–29 (1959).
Vannikov et al. "Antihypoxic effect of PSN", Tkanevaya Gipoksiya Ee Korrekts pp. 4–27 (1981).
Vannikov et al. translation of "Antihypoxic effect of PSN", Tkaneraya Gipoksiya Ee Korrekts pp. 4–27 (1981).
Lokshina et al., Med. Radiol 12(2), pp. 81–83 (1967).

*Primary Examiner*—Jeffrey C. Mullis
*Attorney, Agent, or Firm*—Banner & Witcoff, Ltd.

[57] ABSTRACT

Aqueous solutions containing peroxodisulfate ions are described for the preparation of medicaments for the treatment of malignant cells of human and animal bodies. Furthermore, a process for the preparation of the agent and a device for carrying out the process are described. The agents are available, for instance, by actinic irradiation of aqueous solutions containing anions of oxygen acids of sulfur, particularly sulfate ions and/or peroxodisulfate ions, and having a pH-value of from 2 to 7.

32 Claims, 1 Drawing Sheet

USE OF AQUEOUS SOLUTIONS CONTAINING PEROXOBISULPHATE IONS FOR THE TREATMENT OF MALIGNANT CELLS

The invention relates to the use of aqueous solutions containing peroxodisulfate ions for the production of medicaments for the treatment of malignant cells of human and animal bodies. Furthermore, a process for the production of the agent and a device for carrying out the process are described.

Already in 1959 O. Warburg has noted in "Partielle Anaerobiose der Krebszellen und Wirkung der Röntgenstrahlen auf Krebszellen" ("Die Naturwissenschaften", vol. 2, 1959, pages 25 ff) that hydrogen peroxide can create a specific damage of cancer cells. Hydrogen peroxide acts at high concentrations as a cell poison. At low concentrations, in which it is found among others as an intermediate of the respiratory chain of the cells, it will be degraded by the enzyme catalase which is present in healthy cells. However, the enzyme catalase is present in cancer cells in only distinctly reduced concentration. Therefore, the therapeutic effect of X-rays is based upon the formation of hydrogen peroxide, which is degraded by catalase in healthy cells, whereas it has the desired damaging effect upon cancer cells. However, besides this effect, there are occuring side effects by using this therapy, which are based upon the known interaction processes of ionizing irradiation with organic tissue, and which are strongly straining the patient. The direct addition of hydrogen peroxide via the bloodstream to the cells to be treated, is impossible, because the catalase of the blood serum degrades the cell poison hydrogen peroxide before it reaches the cells to be cured.

From DE 35 28 379 A1 agents are known for the treatment of aqueous systems as well as for the regeneration of body cells, especially skin cells, which represent an aqueous medium containing peroxodisulfate ions. Among others, the agents are used for regeneration, i.e. for restoring body cells, particularly skin cells. The topical application is described for Psoriasis and diabetic gangrene.

DE 36 27 759 A1 discloses pharmaceutical compositions for the inactivation of bacterial endotoxins which contain a nontoxic water-soluble pharmaceutically acceptable peroxodiphosphate compound as an active substance.

From DERWENT-Abstracts 86-02462/04=PT 80 707 A is known, that derivatives of peroxodiphosphonic acid inhibit the development of tumor cells upon oral or systematic administration. The compound is added to a salt solution in a phosphate buffer at pH from 7 to 7,4, or in the form of coated tablets which do not disintegrate in the stomach but disintegrate by influence of the intestinal liquid.

On the other hand, the object of the present invention consists in providing and using a specifically acting agent for the treatment of malignant cells.

FIG. 1 depicts the preparation of the aqueous solutions in accordance with the present invention.

A primary embodiment of the present invention consists in the use of aqueous solutions containing peroxodisulfate ions for the preparation of medicaments for the treatment of malignant cells of the human or animal body.

A further embodiment of the present invention consists in the preparation of the aforementioned solutions which are available for instance by actinic irradiation of aqueous solutions containing anions of oxygen acids of sulfur, particularly sulfate ions and/or peroxodisulfate ions, having a pH value of 2 to 7.

The concentration of peroxodisulfate ions in the aqueous solutions to be applied in the present invention, are normally extremely low, because the peroxodisulfate ions are toxic at high concentration. Therefore, in another embodiment of the present invention, it is preferred that the solutions contain from $10^{-5}$ to $10^{-11}$ g/l, in particular from $10^{-7}$ to $10^{-11}$ g/l, peroxodisulfate ions. The concentration of peroxodisulfate ions should not exceed $10^{-4}$ g/l.

It can be achieved by agents of this kind, that the cells of the cell tissue to be treated, can be reached via the bloodstream, before they are degraded by endogenous enzymes like catalase. The desired degradation of the agents is not happening before they are enriched in the cells, such that hydrogen peroxide is produced intracellularly and will produce there the desired effect. Therefore, requirements to be met by the agents are such, that they are not attacked, or attacked only to a limited degree, by the catalase and that they degrade in a sufficiently slow way in the desired manner, such that the intracellular formation of the hydrogen peroxide is assured.

The agent is available in a preferred embodiment of the present invention by irradiation with light of a wavelength from 190 to 700 nm, particularly UV light. The duration and intensity of irradiation can be adjusted for instance by means of the device according to the invention by dilution and irradiation.

A further preferred embodiment of the present invention is working on the principle, that the diluted aqueous solutions contain anions of oxygen acids of sulfur in an amount of from $10^{-2}$ to $10^{-4}$ g/l before the irradiation. Due to the fact that also after termination of the irradiation of solutions containing sulfate ions, still a certain amount of sulfate ions will remain, it is preferred that the agent for the treatment of malignant cells contain sulfate ions after the irradiation in a practically non detectable amount, i.e. at the most of $10^{-6}$ g/l.

By the aforementioned actinic radiation a variety of reaction products will be produced from the anions of the oxygen acids of sulfur. Among others peroxodisulfate ions could be detected.

The solutions to be used are relatively unstable, such that they should be administered immediately to the patient, if possible. However, in a particularly preferred embodiment of the present invention, it is preferred to add stabilizers for peroxi compounds to the agents. Particularly preferred according to the invention is ethanol as a stabilizer, particularly in an amount of 15% by weight relating to the aqueous solution. Moreover, hydrogen peroxide has been proven too, to be a stabilizer for the agents to be applied. However, due to the toxicity, it is hereby necessary to apply small amounts e.g. less than 1,5% by weight in relation to the aqueous solution.

For oral application, it is particularly preferred to adjust the pH value of the agent according to the invention in the range of less than 7, particularly from 4 to 5. However, besides this, the sublingual or parenteral, that is intratumoral, intramuscular or intravenous application is also possible in the same manner. In an alternative preferred embodiment, the solution is stabilized with up to 1.5% ethanol and 1.5% hydrogen peroxide, both by weight of solution.

Aqueous solutions of these agents that are introduced into the bloodstream in a suitable concentration, can be transported for the moment by the blood without significant degradation. They are entering step by step into the interior of healthy as well as diseased cells. In healthy cells, hydrogen peroxide molecules formed by hydrolytic degradation, will be degraded immediately by the enzyme catalase being present in a sufficient amount without damaging the cells. In the malignant cells having a reduced amount of this enzyme, an enrichment of the solution can occur, which finally leads to the destruction of the malignant cells or at least delays or completely inhibits their division.

The preparation of solutions applicable in medicine, is preferably made by a hereinafter described device, whereby diluted solutions containing the anions of oxygen acids of sulfur, particularly sulfuric acid, are streaming in distilled water through a system of tubes, whereby they are continuously diluted and irradiated by actinic light, for instance by UV light.

Details of this kind of preparation of the agents will be illustrated by means of the FIGURE.

1 represents a block, wherein the preparation of ultra pure water takes place, from which the invention is starting. Conveniently, the preparation of ultra pure water is realized by gradually executing the following process steps: demineralization, distillation, UV-irradiation of the vapor during distillation. This irradiation is serving for the complete sterilization of the water.

The ultra pure water is fed via a filter 2 to a storage jar 3. This storage jar 3 is equipped with a filling level sensor 4, the signals of which are transferred to a controlling device 5. The preparation of ultra pure water is made in relation to the filling level. For that purpose the block 1 is connected via a control line with the control device 5.

The electrical conductance of ultra pure water is controlled by measurement. For that purpose a electrical conductance meter is installed in the line running from the block 1 to the storage jar. This one too, is transferring its signals to the central control device 5. The ultra pure water should have an extremely low electrical conductance (as measured in Siemens, S), that is in the range of µS.

The actual preparation of the agent takes place in the containers 7 to 11. In this container are placed an irradiation tube 13 to 17, respectively, from which light in the IR to UV region is emitted, for instance a "UV-Wasserklärer" (UV sterilizer) from the Company Wiegandt (Krefeld) 30 W, 220/230 V, ca. 50 Hz, length of ca. 1 m.

The diluted, aqueous solution is streaming through the space having a circular cross section, formed by the containers 7 to 11 and by the irradiation tubes 13 to 17, axially arranged therein. The dimensions are selected in a way, that about 6 ml of water per 1 cm are contained in the container 7 to 11.

The way of voltage supply to the tubes 13 to 17 is not represented in detail. Conveniently, it is also operated by the control device.

In order to get a flow and dilution, ultra pure water from the storage jar 3 is delivered to every containers 7 to 11 via pump 18, preferably a flow inducer. The flow rate of the liquid to be irradiated in the container 7 to 11 should be relatively low. This will be achieved by adjusting the flow in the individual lines leading to the containers 7 to 11 to 100 ml/h. The rate is generally depending upon the type, quantity and size of the tubes. It is important that the solution will receive its oxidizing characteristics.

Additionally, a certain amount of for instance sulfate ions in aqueous solution from the storage jar 19 is added to the first container 7 situated in the flow direction. The feeding is accomplished in a discontinuous way and it is controlled by valve 21. The operation of this valve is done again by means of the control device 5.

The irradiation and dilution process which serves for the preparation of the agent will start after addition of a certain amount of the sulfate ions.

The solution arriving at container 7, will be diluted with the ultra pure water flowing therein. The solution is entering into the second container 8 after having been flowed through the first container 7. Therein, irradiation and dilution are continued by addition of more ultra pure water. This procedure is continued in the additional containers 9 to 11. The solution is leaving the last container 11 and will be fed via line 22 to the storage jars 23, 24, 25 in a way which will be described hereinafter.

The storage jars 23, 24, 25 are connected to line 22 via valves 26, 27, 28. These valves are conveniently formed as electromagnetic valves, such that they can be operated by means of the control device 5.

Furthermore, the storage jars 23, 24, 25 are equipped with filling level sensors 31, 32, 33, which are connected also with the control device 5 in a way not described herein in detail. Finally, the vacuum pump 34 which will produce a vacuum of about 200 to 300 mbar, is attached to the containers 23, 24, 25. A measuring device 35 is provided to control this pressure, the signals of which are transferred to the control device 5 too.

Sensors, respectively, measuring devices are situated in line 22, by which the temperature (36), pH-value (37) and filling level (38) can be controlled. The signals delivered by the the sensors 36, 37, 38, are transferred again to the control device 5.

The irradiation and dilution process will start after addition of the determined amount of sulfate ions from the storage jar 19 into the first irradiation container 7. When a solution of $H_2SO_4$ is used, it is convenient that the latter is present in a concentration of $10^{-2}$ g/l.

The substance ($H_2SO_4$) added to container 7, is not still present in the solution leaving container 11 immediately after the start of the production process. One has to wait until it is perceptible by means of the measuring devices 36 to 38, that the liquid leaving the container 11 contains sulfate ions. Up to that time, the valves 27 and 28 are closed and the valve 26 is open. The liquid leaving this valve 26 is discarded.

The valve 26 will not be closed, before the sulfate ion concentration in the liquid leaving the last irradiation container 11 amounts to about $10^{-5}$ to $10^{-6}$ g/l. By opening valve 27 one will achieve that this solution will flow into the storage jar 24. After this, the concentration of sulfate ions will decline in a continuous manner. Conveniently, the valves 26, 27, 28 have to be controlled in such a way that solutions of varying concentrations will reach the storage jars 23, 24, 25, such that for instance a sulfate concentration of about $10^{-5}$ g/l will be present in storage jar 23, a concentration of about $10^{-6}$ will be present in storage jar 24, and a concentration of about $10^{-7}$ g/l will be present in storage jar 25, whereas the concentration of peroxosulfate ions will increase in the same manner. The solution that has been flown into storage jar 24, can also be used as starting solution by feeding it to the first container 7 (instead of the liquid contained in storage jar 19). The required degree of dilution can be attained faster by this way. The actual agent will be collected in storage jar 25. The processed solution will flow therein, until its concentration of peroxodisulfate ions is about $10^{-5}$ to $10^{-11}$.

The actual flow-through-process needs about 15 hours. After this, about 4,2 l of the agent according to the invention will be available.

The described device permits a discontinuous operation. In order to enable the production of the agent according to the invention in a continuous way, it is convenient, to introduce another device of the described type, and to attach this one to the first irradiation container 7. In the FIGURE, such an additional device is merely illustrated as a block 39 which is attachable via valve 40 to the storage jar 7. If the starting substance of the first plant 39 possesses a suitable concentration (i.e. $10^{-6}$ g/l), then connection with the supplier plant 39 will occur via valve 40. By means of not depicted lines, the starting substance of the supplier plant 39 will be collected in container 23, as long as the concentration of $10^{-6}$ g/l has not been achieved. At a concentration of about $10^{-9}$ g/l of the solution flowing out from container 11, the first irradiation container of the supplier plant 39 must be provided with starting solution from container 19. Thereafter, both plants are separated from each other until the solution leaving the supplier plant will have the concentration, that is necessary for the connection. Container 24 can be omitted using this type of operation. The agent according to the invention will flow again into the container 25.

Another advantage of using a supplier plant 39 consists in the fact that the process of irradiation and dilution will always start from a new (still untreated) substance.

For the preparation of the agents according to the invention, the physical conditions under which the process of dilution and irradiation will proceed, are of special importance. The temperature should be as low as possible, for instance at room temperature or in the range of 40° C. This temperature will be controlled by means of measuring device 36. In the case of increasing temperature on behalf of the heat produced by the irradiation tubes 13 to 17, the not represented cooling equipment, for instance a ventilator, has to be switched on.

Vacuum pump 34 produces a vacuum which will amount to some hundreds millibar. This vacuum causes on the one hand the desired transport of the solution along the device. On the other hand, the solution will release dissolved gases ($CO_2$, $O_2$) or the like. Finally, gas can be fed to the first irradiation container 7 due to the effect of the vacuum pump 34, which will cause turbulence in all containers. Conveniently, pure air will be supplied. The purification of the supplied air will be effected by filter 41.

By using diluted sulfuric acid as a starting substance, the pH values of the agents are, depending on the concentration of sulfate ion, in the range of about 4,5 to 6,5. The electrical conductance is between 100 and 400 µS.

By assistance of control device 5 it is possible to automatize the proceeding of the process. The measuring devices 6, 35, 36, 37, 38 are connected with the unit 5 via signalling lines. The delivered signals are conditioned and serve for controlling the apparatus and components (means 1 to 4 for the production of the starting material, feed pump 18, valves 21, 26, 27, 28, 39, vacuum pump 34), which serve for the proceeding of the production process, and which for their part are connected via control lines with unit 5. In the case of having set a supplier plant 39 before the illustrated plant, then the concentration of the starting material of this supplier plant must also be monitored and the valve 40 before unit 5 must be controlled.

Another embodiment of the present invention concerns the treatment of malignant cells of the human and animal body with aqueous solutions containing peroxodisulfate ions.

EXAMPLES

Example 1

A patient A, who was treated since 1988 because of a recurrent malignant bladder tumor, got again and again a tumor relapse in spite of repeated electroresections. The urologist in charge considered a total bladder resection due to the danger of perforation and/or the danger of tumor metastasizing. In the middle of May 1988, for the first time a treatment with a diluted aqueous solution was carried out, which was prepared according to the present invention and which contained $10^{-6}$ g/l peroxodisulfate ions. The patient took 3×1 teaspoon daily. At a cystoscopic control which was performed 8 weeks later, the bladder mucous membrane appeared completely normal. Since this time mirror controls were performed regularly every 3–4 months. A tumor relapse could no more be detected. It concerns to a recurrent, papillary, uroepithelic carcinoma.

Example 2

The examination of a patient B resulted in strong suspicion of ductal carcinoma in the left breast. A stamping puncture of the suspicious knot confirmed the diagnosis. The recommended mastoamputation was refused by the patient. The regular intake of daily 3×1 teaspoon of a diluted aqueous solution, which was prepared according to the present invention, and which contained $10^{-6}$ g/l peroxodisulfate ions, resulted in a slow retrogression of the knot. Mastographic controls, which were performed half-yearly, confirmed the palpatory findings. The last radiological control after two years of treatment resulted in the following judgment: histologically proven intraductal carcinoma of the left mamma sub alternative therapy. In comparison with the pre-examination, no indication of maligno-typical structures of the left mamma.

Example 3

A heptacellular carcinoma with extensive lung metastasizing was diagnosed with a patient C. After performing the therapy according to examples 1 and 2, a general shot taken from the thorax showed a clear retrogression of the lung round foci, which at the most were obvious in outlines. Judgment: remittance by known lung metastasizing.

Example 4

A mastocarcinoma in the outer upper quadrant of the left mamma was diagnosed with patient D in January 1989. A control shot taken one month later, showed an increase in size of the tumor. After this, a therapy was performed with daily 3×1 teaspoon of a diluted aqueous solution, which was prepared according to the present invention, and which contained $10^{-8}$ g/l peroxodisulfate ions. Control mammographies, which were regularly performed at intervals of 4–5 months resulted in a slow retrogression of the tumor. After 9 months, the focus shadow was clearly reduced to almost one half of it. The control mammography from October 1991 showed only a slight tissue densification, which is imposing only in form of a cicatrix tissue.

We claim:

1. A method for treating malignant cells in a human or animal, comprising administering to the human or animal an effective amount of an aqueous solution containing peroxodisulfate ions in an amount of from $10^{-5}$ to $10^{-11}$ g/l.

2. The method according to claim 1, wherein the solution contains from $10^{-7}$ to $10^{-11}$ g/l peroxodisulfate ions.

3. The method according to claim 1, wherein the solution containing peroxodisulfate is obtained by actinic irradiation of an aqueous solution having a pH-value from 2 to 7 and containing anions of oxygen acids of sulfur.

4. The method according to claim 2, wherein the solution containing peroxodisulfate is obtained by actinic irradiation of an aqueous solution having a pH-value from 2 to 7 and containing anions of oxygen acids of sulfur.

5. The method according to claim 1, wherein the solution containing peroxosulfate is obtained by actinic irradiation of aqueous solutions containing $10^{-2}$ to $10^{-4}$ g/l sulfate ions before the irradiation.

6. The method according to claim 2, wherein the solution containing peroxosulfate is obtained by actinic irradiation of aqueous solutions containing $10^{-2}$ to $10^{-4}$ g/l sulfate ions before the irradiation.

7. The method according to claim 3, wherein the aqueous solution having a pH-value from 2 to 7 contains $10^{-2}$ to $10^{-4}$ g/l sulfate ions before the irradiation.

8. The method according to claim 4, wherein the aqueous solution having a pH-value from 2 to 7 contains $10^{-2}$ to $10^{-4}$ g/l sulfate ions before the irradiation.

9. The method according to claim 1, wherein the aqueous solution containing peroxodisulfate ions contains stabilizers.

10. The method according to claim 2, wherein the aqueous solution containing peroxodisulfate ions contains stabilizers.

11. The method according to claim 3, wherein the aqueous solution containing peroxodisulfate ions contains stabilizers.

12. The method according to claim 4, wherein the aqueous solution containing peroxodisulfate ions contains stabilizers.

13. The method according to claim 5, wherein the aqueous solution containing peroxodisulfate ions contains stabilizers.

14. The method according to claim 6, wherein the aqueous solution containing peroxodisulfate ions contains stabilizers.

15. The method according to claim 7, wherein the aqueous solution containing peroxodisulfate ions contains stabilizers.

16. The method according to claim 8, wherein the aqueous solution containing peroxodisulfate ions contains stabilizers.

17. The method according to claim 1, wherein the pH-value of the solution containing peroxosulfate is adjusted to a range of 4 to 5.

18. The method according to claim 2, wherein the pH-value of the solution containing peroxosulfate is adjusted to a range of 4 to 5.

19. The method according to claim 3, wherein the pH-value of the solution containing peroxosulfate is adjusted to a range of 4 to 5.

20. The method according to claim 4, wherein the pH-value of the solution containing peroxosulfate is adjusted to a range of 4 to 5.

21. The method according to claim 5, wherein the pH-value of the solution containing peroxosulfate is adjusted to a range of 4 to 5.

22. The method according to claim 6, wherein the pH-value of the solution containing peroxosulfate is adjusted to a range of 4 to 5.

23. The method according to claim 7, wherein the pH-value of the solution containing peroxosulfate is adjusted to a range of 4 to 5.

24. The method according to claim 8, wherein the pH-value of the solution containing peroxosulfate is adjusted to a range of 4 to 5.

25. The method according to claim 9, wherein the pH-value of the solutions are adjusted to a range of 4 to 5.

26. The method according to claim 10, wherein the pH-value of the solutions are adjusted to a range of 4 to 5.

27. The method according to claim 11, wherein the pH-value of the solutions are adjusted to a range of 4 to 5.

28. The method according to claim 12, wherein the pH-value of the solutions are adjusted to a range of 4 to 5.

29. The method according to claim 13, wherein the pH-value of the solutions are adjusted to a range of 4 to 5.

30. The method according to claim 14, wherein the pH-value of the solutions are adjusted to a range of 4 to 5.

31. The method according to claim 15, wherein the pH-value of the solutions are adjusted to a range of 4 to 5.

32. The method according to claim 16, wherein the pH-value of the solutions are adjusted to a range of 4 to 5.

\* \* \* \* \*